(12) United States Patent
Rolli

(10) Patent No.: US 8,082,639 B2
(45) Date of Patent: Dec. 27, 2011

(54) METHOD FOR PRODUCING A TAMPON WRAPPED IN A PROTECTIVE COVER

(75) Inventor: Kilian Rolli, Würenlingen (CH)

(73) Assignee: RUGGLI Projects AG, Hagendorn-Cham (CH)

( * ) Notice: Subject to any disclaimer, the term of this patent is extended or adjusted under 35 U.S.C. 154(b) by 412 days.

(21) Appl. No.: 11/989,971

(22) PCT Filed: Aug. 2, 2006

(86) PCT No.: PCT/EP2006/007659
§ 371 (c)(1),
(2), (4) Date: Sep. 10, 2009

(87) PCT Pub. No.: WO2007/017173
PCT Pub. Date: Feb. 15, 2007

(65) Prior Publication Data
US 2010/0088867 A1 Apr. 15, 2010

(30) Foreign Application Priority Data
Aug. 5, 2005 (DE) .......................... 10 2005 037 065

(51) Int. Cl.
*A61F 13/20* (2006.01)
(52) U.S. Cl. ........................................................ 28/118
(58) Field of Classification Search ............... 28/118, 28/119, 121, 122, 120; 493/407, 464, 967, 493/386, 387, 390, 156; 53/436, 438, 439, 53/523, 526–529; 604/904, 385.02, 385.17
See application file for complete search history.

(56) References Cited

U.S. PATENT DOCUMENTS

| 3,766,703 A | | 10/1973 | Simon et al. | |
| 4,340,055 A | * | 7/1982 | Sneider | 28/118 |
| 4,610,659 A | * | 9/1986 | Friese | 604/11 |

(Continued)

FOREIGN PATENT DOCUMENTS

DE   11 65 809   3/1957

(Continued)

OTHER PUBLICATIONS

International Search Report.

*Primary Examiner* — Amy Vanatta
(74) *Attorney, Agent, or Firm* — Collard & Roe, P.C.

(57) ABSTRACT

A method is proposed for producing a tampon (T) packaged in a protective sleeve made from a preform (V) which is preferably formed by winding a strip of fibrous non-woven material. The preform (V) is shaped to form the tampon in separate pressing stages by pressure forces acting on it from outside, and is individually packaged by providing it with a film sleeve (10) tightly enclosing the tampon (T) serving as a protective sleeve.

Figure 4:
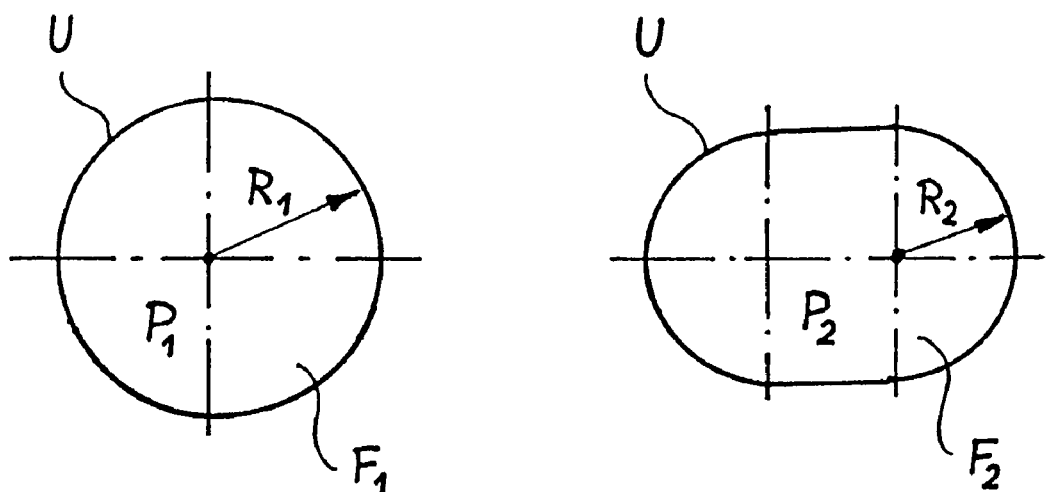

In order to reduce the complexity involved in producing a tampon, and in particular a non-round tampon, to the point at which its is individually packaged in the protective sleeve, the substantially cylindrical preform (V) is already paced in the film sleeve (10) surrounding at least the external surface of the preform (V) before the final forming stage (15). The preform (V) including the film sleeve (10) surrounding it is then fed to the final stage (15), where it is formed between at least two pressing jaws (20*a*, 20*b*) which can be displaced relative to on another until it has assumed its final non-cylindrical shape.

6 Claims, 2 Drawing Sheets

| U.S. PATENT DOCUMENTS | | | |
|---|---|---|---|
| 6,299,573 B1 * | 10/2001 | Hull et al. | 493/464 |
| 6,310,269 B1 | 10/2001 | Friese et al. | |
| 6,465,713 B1 | 10/2002 | Gell et al. | |
| 6,537,414 B1 | 3/2003 | Schoelling | |
| 6,889,409 B2 | 5/2005 | Friese et al. | |
| 6,953,456 B2 | 10/2005 | Fuchs et al. | |
| 7,059,026 B2 | 6/2006 | Friese et al. | |
| 2002/0133135 A1 | 9/2002 | Gell et al. | |
| 2002/0147436 A1 | 10/2002 | Gell et al. | |
| 2003/0075278 A1 | 4/2003 | Schoelling | |
| 2004/0226152 A1 * | 11/2004 | Prosise et al. | 28/118 |
| 2005/0027275 A1 * | 2/2005 | Wasson et al. | 604/385.01 |
| 2005/0096620 A1 * | 5/2005 | Awolin et al. | 604/385.18 |
| 2006/0185136 A1 | 8/2006 | Friese et al. | |
| 2009/0259165 A1 * | 10/2009 | Minoguchi et al. | 604/11 |

| FOREIGN PATENT DOCUMENTS | | |
|---|---|---|
| DE | 18 08 848 | 6/1970 |
| DE | 18 15 541 | 7/1970 |
| DE | 18 15 374 | 9/1970 |
| DE | 19 55 600 | 5/1971 |
| DE | 39 34 153 | 4/1991 |
| DE | 200 02 337 | 5/2000 |
| DE | 200 22 800 | 9/2002 |
| DE | 698 07 642 | 2/2003 |
| DE | 600 05 672 | 8/2004 |
| EP | 1 010 622 | 6/2000 |
| WO | WO 01/01910 | 1/2001 |
| WO | WO 02/070026 | 9/2002 |
| WO | WO 03/007862 | 1/2003 |
| WO | WO 2004/100847 | 11/2004 |

* cited by examiner

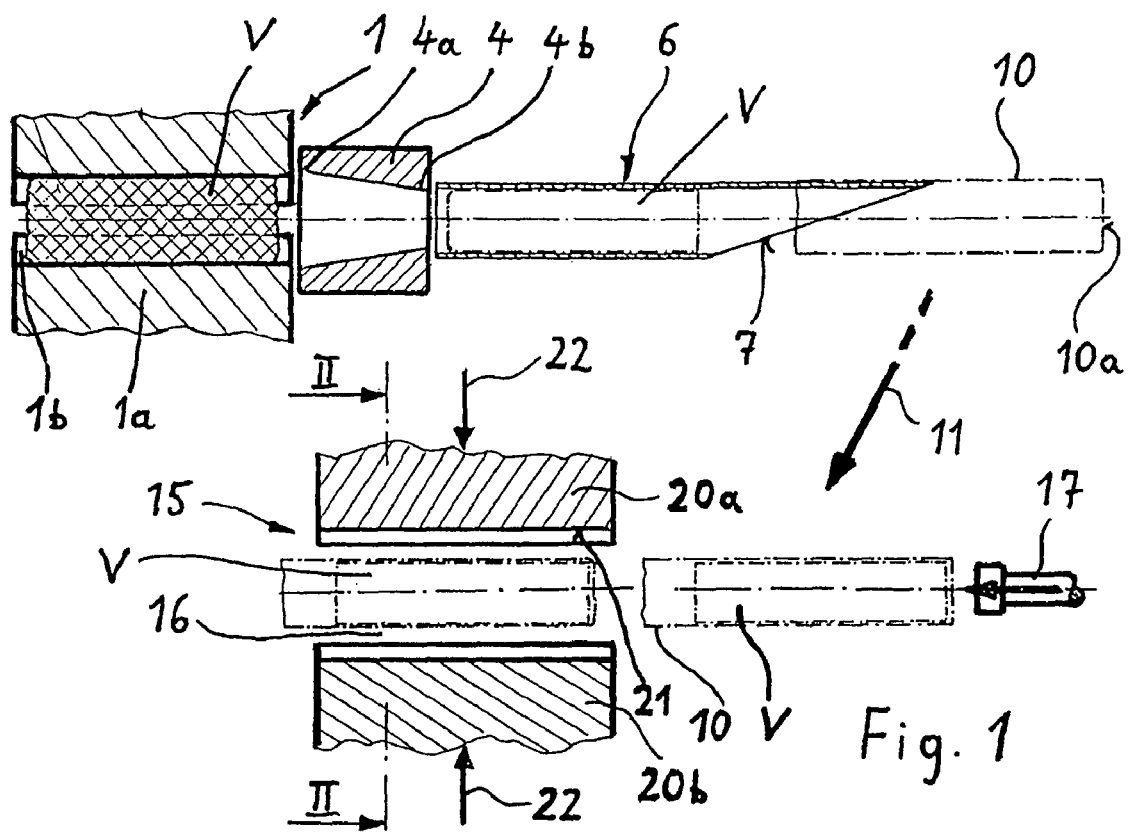
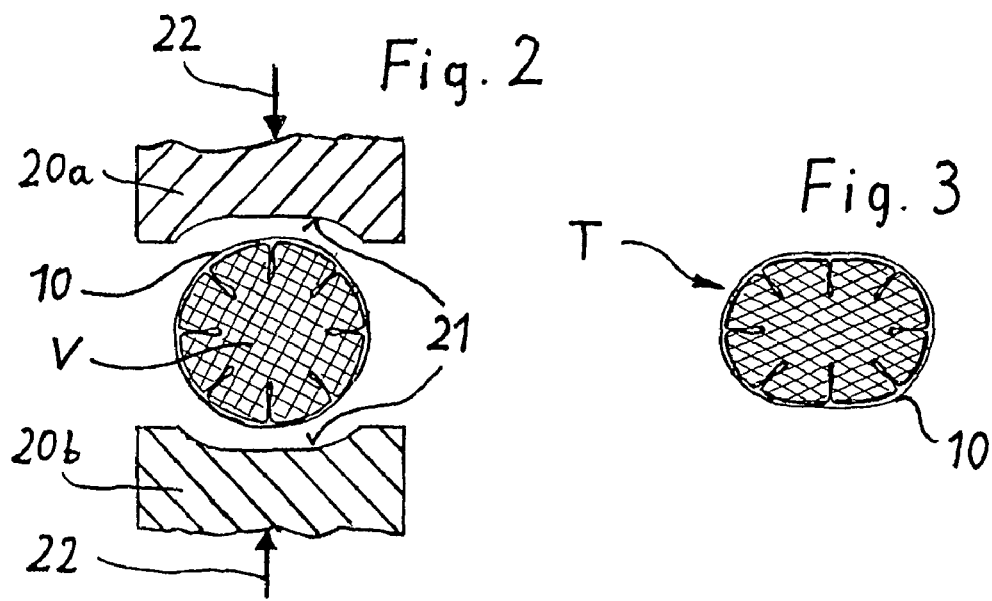

METHOD FOR PRODUCING A TAMPON WRAPPED IN A PROTECTIVE COVER

CROSS REFERENCE TO RELATED APPLICATIONS

Applicant claims priority under 35 U.S.C. §119 of German Application No. 10 2005 037 065.9 filed Aug. 5, 2005. Applicant also claims priority under 35 U.S.C. §365 of PCT/EP2006/007659 filed Aug. 2, 2006. The international application under PCT article 21(2) was not published in English.

The invention relates to a method of producing a tampon packaged in a protective sleeve, made from a preform preferably formed by winding a strip of fibrous non-woven material, which is shaped to form the tampon in separate forming stages by means of pressure forces acting on the preform from outside, and which is individually packaged by providing it with a film sleeve tightly enclosing the tampon serving as a protective sleeve.

A widely known method of producing tampons (menstruation tampons) is known from patent specification DE 39 34 153 C2. In this instance, the process of pressing the preform made from a wound strip of fibrous non-woven material takes place in several stages. During a first stage, forming takes place by means of two groups of pressing jaws which can be fed centripetally with respect to the longitudinal axis and are provided with pressing edges in order to impart to the preform the shape of a ribbed tampon with longitudinal grooves and ribs disposed in between. By means of a ram, the preform is axially ejected from the pressing jaws, which remain in the closed a or slightly open position, and is pressed by means of an adjoining forming tool. This forming tool is of a conical design with an inlet diameter corresponding to the external diameter of the preform and an outlet diameter corresponding to the final external diameter of the tampon.

For packaging and hygiene purposes, the tampon is then provided with a protective sleeve, which tightly encloses the tampon. The protective sleeve is cut from a sleeve of film. As the tampon is being inserted in the film sleeve, the essentially cylindrical shape of the tampon facilitates the process of introducing it axially into the film sleeve, which is likewise cylindrical. In order to finish the protective sleeve, the film sleeve then has to be closed, for which purpose suitable methods are described in patent specifications DE 19 55 600 C1 and EP 1 010 622 A1, for example.

The methods outlined above can be used to produce and package virtually all tampons of a substantially circular cross-section. However, tampons with a cross-sectional surface other than a circular shape have already been proposed, for example in patent specification DE 18 15 374 A, for example tampons with slightly elliptical or oval cross-sections. Introducing such tampons into a prefabricated film sleeve requires more complex apparatus.

The underlying objective of the invention is to reduce the complexity involved in producing a tampon, and in particular a tampon that is not round, to the point at which its is individually packaged in a protective sleeve.

In order to achieve this objective, a method of the type outlined above is proposed, whereby the substantially cylindrical preform is already placed in the film sleeve surrounding at least the external surface of the preform before the final forming stage, and the preform including the film sleeve surrounding it is then fed to the final forming stage, where it is formed between at least two pressing jaws which can be moved relative to one another until it has assumed a non-cylindrical final shape.

The invention is therefore based on the principle of providing the tampon with the film sleeve even before performing the last, i.e. final shaping process. Only then is the preform fed to the final forming stage. This final process of applying pressure takes place between at least two pressing jaws which can be moved relative to one another and continues until the final non-cylindrical cross-sectional shape is imparted to the tampon. This being the case, use is made of the fact that, taking a predefined cross-sectional surface, the circumference extending round this surface is at its smallest if the surface is a circular surface. Conversely, changing a circular cross-section into a different cross-sectional shape whilst keeping the circumference constant leads to a reduction in cross-section and, provided a volume is enclosed, to a compaction of the surrounded material. The final pressing stage proposed by the invention therefore causes an additional compaction of the fibrous material in the tampon, provided a film material with a sufficiently low stretching capacity is used.

In the case of one embodiment of the invention, it is proposed that the two ends of the film sleeve be closed before the preform including the film sleeve completely surrounding it is fed to the final forming stage. However, of even greater advantage is a sequence whereby the two ends of the film sleeve are not closed until after the preform has been shaped between the pressing jaws to its final shape.

In terms of the film sleeve, the aim is to opt for a film material that has as low a stretching capacity as possible. In one embodiment, a film material with a base of cellophane or polypropylene is proposed for this purpose.

Other details and advantages will become apparent from the following description of an example of an embodiment, illustrated in the appended drawings. These specifically illustrate the following:

FIG. 1 a schematic diagram of the main components of a device for pressing and individually packaging tampons;

FIG. 2 a cross-section on a larger scale along plane II-II indicated in FIG. 1, including a tampon preform enclosed by a film sleeve;

FIG. 3 the finished tampon after it has passed through the final pressing stage and FIG. 4 a mathematical illustration of the forces at play in the compaction of the tampon cross-section and once the final pressure has been applied.

The device illustrated on a simplified basis in FIG. 1 enables the method proposed by the invention to be implemented. Reference number 1 denotes a pressing tool which, in the embodiment illustrated as an example here, is made up of eight pressing jaws 1a displaceable in the radial direction. The pressing jaws 1a are provided with pressing surfaces and also each have a pressing edge 1b, each of which projects even farther in the radial direction. When the pressing jaws 1a of the pressing tool have been closed after introducing a blank of any cross-sectional shape made from absorbent fibres, a preform V is produced with a core of higher density and a peripheral zone of axially extending ribs and longitudinal grooves extending between the ribs which will improve the absorption behaviour of the subsequently finished tampon.

The preform V is axially ejected from the pressing tool 1 by means of an ejector ram, although this is not illustrated in the drawing. Disposed after the pressing tool 1 in the ejection direction is a forming tool 4 with a conically tapering internal contour. The inlet diameter 4a of the forming tool 4 is the same as or slightly bigger than the external diameter of the preform V. The outlet diameter 4b of the forming tool 4 defines the external diameter of the preform as it leaves the forming tool 4, its diameter being thus further reduced. The forming tool 4 therefore represents the second forming stage for the preform V.

Adjoining the outlet diameter 4b of the forming tool 4, again in the ejection direction, is an albeit thin-walled but rigid guide sleeve 6, which tapers out at its other end in a ramp 7.

From the other end, i.e. from the right-hand side of FIG. 1, a cylindrical film sleeve 10 prefabricated elsewhere can be pushed axially onto the ramp 7 of the thin-walled guide sleeve 6. The film sleeve 10 is a cylindrically smooth, non-profiled sleeve made from a cellophane film or polypropylene film that is impervious to moisture. At its rear end, denoted by 10a, it may already have a sealed closure, e.g. by heat sealing. The front, rounded end is then closed, preferably also by heat sealing. Within the context of the invention, the film material used for the film sleeve 10 should have a relatively low stretching capacity, i.e. a low expansion behaviour under tensile load, at least in the circumferential direction.

In order to enclose the preform V completely with film material, the film sleeve 10 is longer than the preform V, even if the rear end 10a has been closed beforehand.

The diameter of the preformed cylindrical film sleeve 10 is only slightly bigger than the diameter of the preform V pushed along the cylindrical guide sleeve 6 to enable the round preform 1 to be pushed into the cylindrically preformed film sleeve 10 unhindered.

As indicated by arrow 11 in FIG. 1, the preform V including the film sleeve 10 surrounding its entire length, is then transferred to a third forming stage, the pressing stage 15. In the third forming stage, the preform V is firstly positioned in alignment with a pressing chamber 16. By means of a ram 17 which is able to move axially in the direction towards the pressing chamber 16, the preform V then arrives in the pressing chamber 16, which is bounded by pressing or pressure plates 20a, 20b on two sides in the embodiment illustrated as an example here. These are able to move relative to one another, for which purpose it is already sufficient if only one of the two pressing or pressure plates is able to move relative to the other.

As may be seen from FIG. 2, each pressure plate 20a, 20b has a pressing or pressure surface 21 with a slight spherical depression. The preform V, which is still substantially cylindrical at this point in time, is positioned centrally between the pressure surfaces 21. As indicated by the pressure arrows 22, the pressure plates 20a, 20b, either one of them or both them, move towards one another, so that the preform V disposed between them is formed again and is so conforming to the contour of the spherical depressions of the pressure surfaces 21. In the example illustrated here, the initially circular cylindrical cross-section of the preform V is shaped to produce a more oval cross-section of the now finished tampon T, as shown by the cross-section illustrated in FIG. 3.

However, it would also be possible to use forming process leading to other non-round cross-sections. Instead of two pressure plates 20a, 20b, it would also be possible to work with three or more pressure plates. Furthermore, forming in the final pressing stage need not necessarily result in a slightly oval cross-section. Depending on the shape of the pressure surfaces 21, forming to produce an elliptical cross-section or other non-round cross-sections would also be possible.

Heating elements may be integrated in the pressure plates 20a, 20b in order to heat the pressure surfaces 21 as they close.

FIG. 4 is a geometrical illustration of the additional compaction of the tampon which takes place in the final forming stage. Since the film material used for the film of the film sleeve has a relatively low stretching capacity, the circumference U of the film sleeve and hence the tampon remain identical before and after the final pressing stage. However, this simultaneously leads to a reduction in the cross-sectional surface from $F_1$ to $F_2$. At the same time, the radius $R_1$ of the circle is reduced to the smaller reference radius $R_2$ of an oval. Since the fibrous material of the tampon enclosed by the film sleeve can not go anywhere else, this results in an additional compaction of the fibrous material accompanied by an increase in the internal pressure from $P_1$ to $P_2$ during the change from a circular cross-section to the oval cross-section.

LIST OF REFERENCE NUMBERS

1 Pressing tool
1a Pressing jaw
1b Pressing edge
4 Forming tool
4a Inlet diameter
4b Outlet diameter
6 Cylindrical guide sleeve
7 Ramp
10 Film sleeve
10a Closed end of the film sleeve
11 Arrow
15 Final forming stage
16 Pressing chamber
17 Ram
20 Pressure plate
20b Pressure plate
21 Pressure surface
22 Pressure arrow
$F_1$ Surface
$F_2$ Surface
$R_1$ Radius
$R_2$ Radius
T (Finished) tampon
U Circumference
V Preform

The invention claimed is:

1. A method of producing a tampon packaged in a protective sleeve, which is made from a preform formed by winding a strip of fibrous non-woven material which is shaped to form the tampon in separate forming stages by pressure forces acting on the preform from outside, and which is individually packaged by providing a film sleeve tightly enclosing the tampon serving as a protective sleeve, wherein
    the film sleeve is produced as a cylindrically smooth, non-profiled sleeve that is impervious to moisture and surrounds at least an external surface of the preform,
    subsequently a substantially cylindrical preform is placed in the film sleeve before a final forming stage, and
    the preform including the film sleeve surrounding the preform is then fed to the final forming stage, where the preform is formed between at least two pressing jaws which can be displaced relative to one another until the preform has assumed a non-cylindrical final shape, and
    the tampon is individually packaged by closing the film sleeve.

2. The method as claimed in claim 1, wherein the preform is formed to an elongate cross-section between the pressing jaws.

3. The method as claimed in claim 1, wherein the pressing jaws are heated.

4. The method as claimed in claim 1, wherein a first end and a second end of the film sleeve are closed before the preform including the film sleeve completely surrounding the preform is fed to the final forming stage.

5. The method as claimed in claim 1, wherein a first end and a second end of the film sleeve are not closed until after the preform has been formed to the non-cylindrical final shape between the pressing jaws.

6. The method as claimed in claim 1, wherein the film sleeve is made from a film material with a base of cellophane or polypropylene having a low capacity to stretch.

\* \* \* \* \*